United States Patent [19]

Hennuy et al.

[11] Patent Number: 4,671,461
[45] Date of Patent: Jun. 9, 1987

[54] DISTRIBUTOR FOR A VAPORIZER AND STEAM DIFFUSER

[75] Inventors: Jean Hennuy; René Seguret, both of Villefranche/Saone, France

[73] Assignee: SEB S.A., Selongey, France

[21] Appl. No.: 755,717

[22] Filed: Jul. 16, 1985

[30] Foreign Application Priority Data

Jul. 25, 1984 [FR] France .................. 84 11789

[51] Int. Cl.⁴ .............................................. B05B 7/12
[52] U.S. Cl. ..................... 239/306; 239/138; 239/417.5; 251/236; 137/881
[58] Field of Search ................................ 239/135–138, 239/600, 317, 318, 124, 127, 446, 447, 312, 407, 417.5, 443, 304, 306; 222/396, 397, 330, 331; 137/881; 251/236

[56] References Cited

U.S. PATENT DOCUMENTS

| | | | |
|---|---|---|---|
| 2,538,211 | 1/1951 | Prout | 239/446 |
| 3,207,443 | 9/1965 | Gilmour | 239/312 |
| 3,761,021 | 9/1973 | White | 239/312 |
| 3,917,172 | 11/1975 | O'Hare | 239/312 X |
| 4,274,588 | 6/1981 | Schwob | 238/138 |
| 4,365,758 | 12/1982 | Schaming | 239/600 |

FOREIGN PATENT DOCUMENTS

| 2460644 | 1/1981 | France. | |
|---|---|---|---|
| 39988 | 6/1965 | German Democratic Rep. | 239/124 |

Primary Examiner—Andres Kashnikow
Assistant Examiner—Mary Beth O. Jones
Attorney, Agent, or Firm—Young & Thompson

[57] ABSTRACT

The vaporizer and steam diffuser according to the invention comprises a sleeve (4) having a steam supply aperture (5), a hollow body (6) disposed in the sleeve (4) and having an aperture (9) for connection between the interior of the body (6) and the interior of the sleeve (4), and at least one first and one second separate output apertures (10, 12), of which one (10) is equipped with a vaporization nozzle (11), at least one separation valve (13) between the output apertures (10, 12), and a means (16) for controlling the position of the valve (13).

12 Claims, 9 Drawing Figures

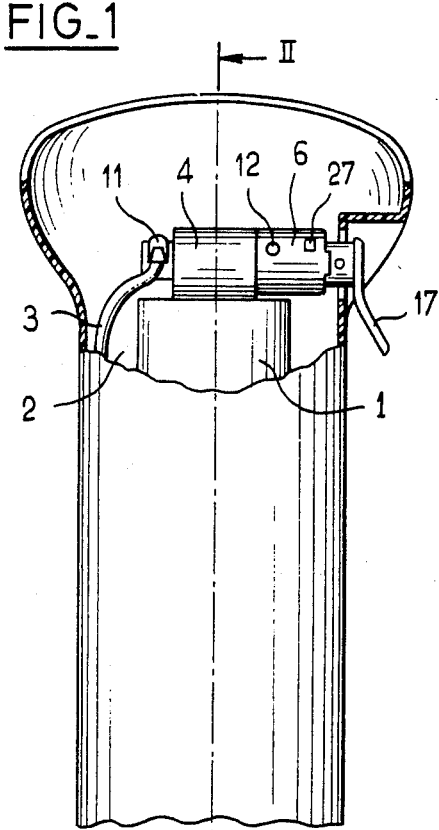
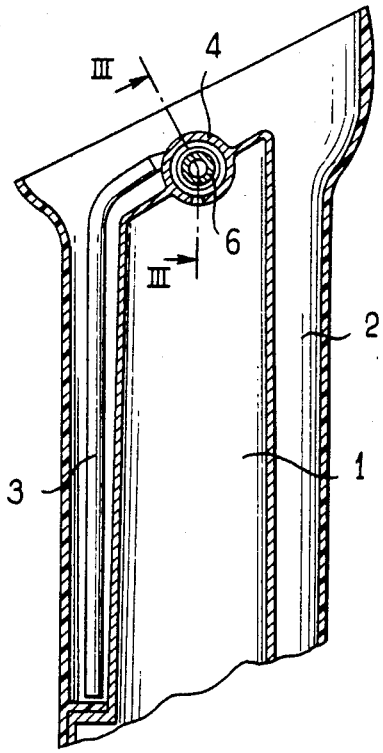
FIG_1
FIG_2
FIG_3

DISTRIBUTOR FOR A VAPORIZER AND STEAM DIFFUSER

The present invention relates to a distributor for a vaporizer and steam diffuser.

Vaporizers, for example lotion vaporizers, are known in which the product to be vaporized is subjected to suction by a steam jet directed substantially at right angles to a duct supplying the product which is to be vaporized. In this case facilities are generally provided for separately diffusing steam for a purpose other than the vaporization. In particular, in the case of an apparatus for treating the skin, and more specifically the skin of the face, it is desirable to have available a source of pure steam, which is generally intended to bring about the dilation of the pores of the skin, whereupon the vaporization of a cold lotion is used to cool the face.

However, in known appliances the function of diffusion of pure steam and the function of vaporization are completely separate, and these appliances therefore have separate operating means, so that their use requires a series of manipulations to pass from one function to another.

A first aim of the present invention is therefore to propose a distributor for a vaporizer-steam diffuser having a construction making it easy to change over from the pure steam diffusion function to the vaporization function, and vice versa, with a minimum of manipulations.

Moreover, vaporization and steam diffusion devices are generally equipped with nozzles having a single orientation, so that the entire appliance must be inclined to follow the contours of the face, which sometimes gives rise to problems in the application of suction to the lotion, particularly when only a small amount of lotion remains in the appliance.

Another aim of the present invention is to propose a distributor for a vaporizer-steam diffuser having a simple construction and making it possible to change the orientation of the jet of steam or the jet of vaporized product without necessarily having to alter the position of the appliance.

For the purpose of achieving the first aim of the invention, a distributor for a vaporizer-steam diffuser is provided which is characterized in that it comprises a sleeve having a steam supply aperture, a hollow body disposed in the sleeve and having an aperture making a connection between the interior of the hollow body and the interior of the sleeve, and at least one first and one second separate outlet apertures, of which one is equipped with a vaporization nozzle, at least one separation valve between the outlet apertures, and a means controlling the position of the valve.

Thus, simply through the operation of the valve with the aid of the control means, the changeover is easily made from the vaporization function to the function of pure steam diffusion, and vice versa.

According to one advantageous version of the invention which seeks to achieve the second aim, the hollow body is mounted for rotation in the sleeve and its position is controlled by a control means common to it and to the valve position control means.

Thus, through the operation of a single control means it is possible to change the orientation of the jet of vaporized product or steam while simultaneously making a change of function.

According to a preferred embodiment of the invention the control means is a sliding rod provided with fastening means for rotation together with the hollow body, one end of the rod being connected to the valve and the other end carrying a control handle. A pull on the control handle therefore effects a changeover from the vaporization function to the pure steam distribution function, or vice versa, while turning the control handle changes the orientation of the jet of vaporized product or pure steam.

According to another aspect of the preferred embodiment of the invention, the control handle is mounted for pivoting about an axis extending crosswise in relation to the control rod and is provided with plates extending transversely of said axis, these plates having a curvilinear edge which is eccentric relative to the pivot axis of the control handle and which is supported on a stop means fastened to the hollow body. By rocking the control handle about the pivot axis the desired function is thus brought into operation and is thus maintained as long as the orientation of the control handle is not changed.

According to another aspect of the preferred embodiment of the invention the means for fastening together the rod and the hollow body in respect of rotation comprise studs which are carried by the rod and extend transversely of the latter and which cooperate with grooves provided in the stop means. The rod is thus enabled to slide with very slight friction, so that the control is easy to operate.

According to yet another aspect of the preferred embodiment of the invention, the valve is disposed between the aperture connecting the interior of the hollow body to the sleeve and the second outlet aperture, while the second outlet aperture has a dimension larger than a steam duct of the nozzle, the nozzle being carried by the first aperture. Thus, when the valve is open the loss of head of the second outlet aperture is less than that of the first outlet aperture, and vaporization is stopped without it being necessary to provide a device for closing the first outlet aperture.

Other characteristics and advantages of the invention will emerge from the description of one non-limitative example given below with reference to the accompanying drawings, in which:

FIG. 1 is a partial view, partly broken away, of a vaporizer and steam diffuser containing the distributor according to the invention;

FIG. 2 is a view in section on the line II—II in FIG. 1;

FIG. 3 is a view of the distributor on a larger scale, in section on the line III—III in FIG. 2;

Referring to FIGS. 1 and 2, the vaporizer and steam diffuser comprises, in the usual way, a chimney 1 connected to a boiler (not shown) for generating steam, usually water vapour, and a lotion container 2, in which a lotion suction tube 3 extends.

Figures 4, 5:
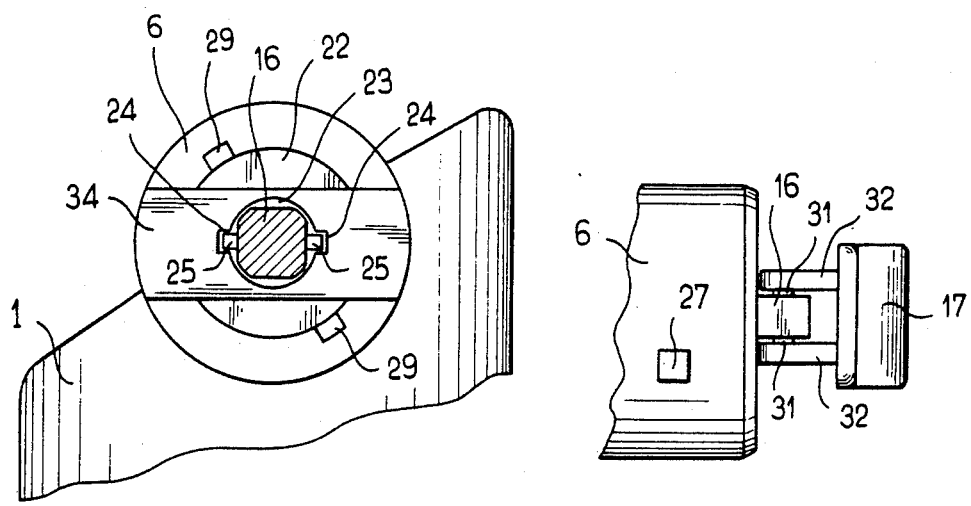
FIG. 4 is a view in section on the line IV—IV in FIG. 3.
FIG. 5 is a top plan view of the control end of the distributor.
Figure 6:
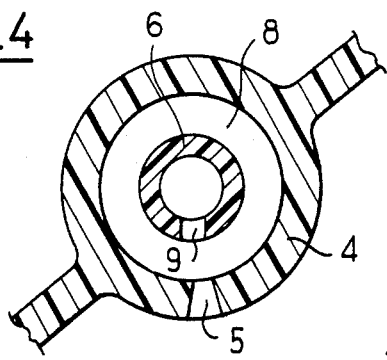
FIG. 6 is a view in section on the line VI—VI in FIG. 3.
Figures 7, 8, 9:
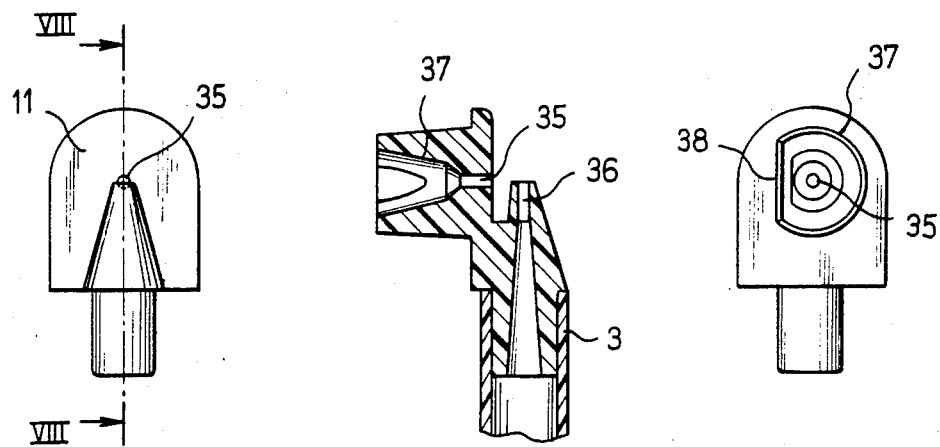
FIG. 7 is a front view of the vaporization nozzle.
FIG. 8 is a view in section on the line VIII—VIII in FIG. 7.
FIG. 9 is a rear view of the vaporization nozzle.

Referring to FIGS. 3 to 9, the distributor according to the invention comprises a sleeve 4 disposed in the top part of the chimney 1, transversely of the latter, and having a supply aperture 5 connecting the interior of the sleeve 4 to the chimney 1.

An elongate hollow body 6 is disposed in the sleeve 4. The hollow body 6 has a circular section with portions having different diameters and has a central duct 7, likewise of circular cross-section and of varying diameter. Adjacent the steam supply aperture 5 the hollow body 6 has an outer diameter slightly smaller than the inner diameter of the sleeve 4 and thus delimits an annular cavity 8. The hollow body 6 has a radial aperture 9 connecting the interior of the hollow body 6 with the interior of the sleeve 4. At one end the hollow body 6 has a first outlet aperture 10 which extends transversely and in which a vaporization nozzle 11 is mounted. A second outlet aperture 12 is provided in the body 6 with the connecting aperture 9 being axially between apertures 10 and 12. A separation valve 13 is disposed across the duct 7, between the outlet apertures 10 and 12, and is provided with a seal 14 bearing against a seat 15 formed by part of the wall of the duct 7. The position of the valve is controlled by a control means comprising a sliding rod 16 fastened to the valve 13 and connected to a control handle 17, which will be described in detail later on.

The hollow body 6 is mounted for rotation in the sleeve 4 with the aid of O-ring seals 18 and 19, disposed respectively in annular grooves 20 and 21 formed in the outer wall of the hollow body 6 with the cavity 8 therebetween. The seals 18 and 19 thus not only form a rotation means for the hollow body 6, but also ensure the sealing of the cavity 8 relative to the outside.

The rotational position of the hollow body 6 is controlled by the rod 16 connected to the handle 17 with the aid of rotational fastening means comprising a stop means 22 through which extends a central channel 23 (FIG. 4) provided with oppositely disposed grooves 24 accommodating studs 25 carried by the rod 16. The stop means 22 is disposed inside the hollow body 6 and is fastened to the latter by studs 26 extending into apertures 27 in the side wall of the hollow body 6. In order to facilitate the introduction of the studs into the body 6, the studs 26 have inclined faces 28 cooperating with complementary inclined surfaces 29 provided at the end of the body 6.

A return spring 30 is disposed between the inner face of the stop means 22 and the valve 13 in order to hold the latter against its seat 15 in the rest position.

The control handle 17 is mounted for pivoting about an axis extending transversely of the control rod 16. This axis is constituted by studs 31 disposed on two opposite sides of the rod 16 (FIG. 5) and engaging plates 32 extending transversely to said axis, these plates having a curvilinear edge 33 whose distance from the pivot axis formed by the studs 31 is variable. The edge 33 bears against a spacer 34 integral with the stop means 22, which is fastened to the hollow body 6 in the manner explained above. The spacer 34 bears by its ends against the periphery of the hollow body 6 and constitutes a stop for the stop means 22 as to its introduction into the hollow body 6.

In the example of embodiment shown in the drawings, the plates 32 have a substantially rectangular periphery, so that in a direction substantially perpendicular to the longitudinal extent of the handle 17 the distance between the studs 31 and the edge 33 is a distance d, while in a direction substantially parallel to the longitudinal extent of the handle 17 the distance between the stud 31 and the edge 33 is a distance D greater than the distance d.

In a manner known per se the nozzle 11 (FIGS. 7 to 9) comprises a steam supply duct 35 whose end discharges near a lotion suction duct 36 extending substantially perpendicularly to the duct 35 and opening at its end remote from the duct 35 into the tube 3 disposed in the lotion container 2. In order to ensure that the tube 3 will be permanently submerged down to the bottom of the lotion container 2, it is desirable to ensure that the positioning of the nozzle 11 is kept as stable as possible. For this purpose a tip 37 is provided which has a flat 38 and a shape corresponding to the opening 10 of the hollow body 6. Thus, when the tip 37 is positioned in the opening 10, it is held in that position with a predetermined orientation.

As illustrated in FIG. 3, the valve 13 is preferably disposed between the connecting aperture 9 and the second outlet aperture 12, and the second outlet aperture 12 has a dimension greater than the duct 35 of the nozzle 11 disposed in the first outlet aperture 10.

The device operates in the following manner: when the handle 17 is in the vertical position shown in FIG. 3, the distance d between the edge 33 of the plates 32 bearing against the stop means 22 and the axis of the studs 31 is sufficiently short to enable the valve 13 to rest on its seat 15. The steam coming from the chimney 1 and flowing through the apertures 5 and 9 then follows the path shown by the arrows in solid lines and escapes through the first outlet aperture 10. Lotion coming from the container 2 is then sucked through the lotion suction duct 36. The direction of the jet of atomized lotion can be varied by the user by operating the control handle 17 so as to pivot the latter about the axis of the conrol rod 16.

When it is desired to obtain steam only, it is sufficient to pivot the control handle 17 about the studs 31 in the direction of the arrow V in FIG. 3, whereupon that portion of the edge 33 of the plates 32 which is at a distance D from the studs 31 comes into contact with the stop means 22. Through this movement the rod 16 is pulled and operates the valve 13 against the action of the spring 30. Because of the substantial difference in loss of head which exists between the duct 35 of the nozzle 11 and the second outlet aperture 12, the steam naturally tends to escape through the second outlet aperture 12, following the path shown by the arrows in broken lines in FIG. 3. As the nozzle 11 is practically no longer supplied with steam, the vaporization of lotion stops immediately. In the same way as in the vaporization position, the orientation of the outlet aperture 12 can be changed by operating the handle 17 so as to pivot it about the axis of the rod 16.

It will be found that the valve 13 also serves as safety valve in the event of excess pressure occurring inside the chimney 1. In this case the valve 13 is in fact pushed back against the action of the spring 30 by the excess pressure existing in the duct 7, and the steam escapes through the second outlet aperture 12.

The invention is obviously not limited to the embodiment described above, and constructional modifications can be made to it.

In particular, although the preferred embodiment of the invention provides for the changeover from the vaporization function to the steam diffusion function to be made by means of a simple valve in conjunction with different dimensions of the first and second outlet apertures, it is possible to provide a double valve disposed on each side of the connecting aperture 9 and having opposite positions for closing the connection to the first outlet aperture on the opening of the connection to the second outlet aperture and vice versa.

Although the rotational fastening means described comprise studs 25 associated with grooves 24, it will be understood that other means may be used; in particular it is possible to provide a rod 16 of square section, introduced into a corresponding square opening in the stop member 22.

We claim:

1. A steam and lotion dispenser comprising:
   a steam container (1),
   a lotion container (2) attached to said steam container,
   a first steam escape aperture (12) on said steam container (1),
   a lotion suction nozzle (36) on said lotion container (2),
   a second steam escape aperture (10) on said steam container (1), said second aperture (10) having a nozzle (11) transversely facing the lotion suction nozzle (36), and
   a distributor comprising closure means (13) disposed intermediate said first and second steam escape apertures, for selectively opening and closing a first path between the steam container (1) and the first steam escape aperture (12) while maintaining opened a second path between the steam container (1) and the second steam escape aperture (10),
   wherein the loss of head in the first path in an open position of the closure means (13) is smaller than the loss of head in the second path.

2. A steam and lotion dispenser according to claim 1 wherein the closure means (13) comprise a valve member (13) which is movable between the open position in which the first path is open, and a closed position in which the valve closes the first path and is exposed to the pressure in the steam container (1) so that, in operation, said pressure tends to move the valve (13) towards its open position against the action of a biasing spring (30).

3. A steam and lotion dispenser according to claim 1, wherein the said first and second steam escape apertures (10, 12) are carried by a hollow body (6) of the distributor, said hollow body (6) being rotatable so as to vary the orientation of the steam escape apertures (10, 12).

4. A steam and lotion dispenser according to claim 3, wherein the hollow body (6) is rotatable in a sleeve (4), and the hollow body (6) and the sleeve (4) define between them an annular chamber (8) communicating with the steam container (1) through an aperture (5) in the sleeve (4) and with the first and second paths through a hole (9) in the hollow body (6).

5. A steam and lotion dispenser according to claim 3, wherein the hollow body (6) and the closure means (13) are operatively connected to a common control means (17) movable in two different directions respectively for actuating the closure means (13) and rotating the hollow body (6).

6. A steam and lotion dispenser comprising:
   a steam container (1),
   a lotion container (2) attached to said steam container,
   a lotion suction nozzle (36) connected to the lotion container (2),
   a hollow body (6) rotatable about one axis and provided with: a steam inlet aperture (9) connected to the steam container (1); a first steam escape aperture (12); and a second steam escape aperture (10) provided with a nozzle (11) tranversely facing the lotion suction nozzle (36),
   a path selection member (13) movably mounted in the hollow body (6) intermediate said first and second steam escape apertures, for selectively closing therein a path between the steam inlet aperture (9) and the first steam escape aperture (12),
   wherein the hollow body (6) and the path selection member (13) are operatively connected to a common control means (17) movable in two different directions respectively for actuating the path selection member (13) and rotating the hollow body (6).

7. Distributor according to claim 6, wherein said second steam escape aperture nozzle (11) has a tip (37) provided with a flat (38), and said second steam escape aperture (10) has a shape complementary to said tip (37).

8. A steam and lotion dispenser according to claim 6, wherein the path selection member (13) is slidable in the hollow body (6) along said one axis and is connected to the control means (17) by a member (16) which is axially slidable in the hollow body (6) and angularly fastened to the hollow body (6) and to the control means (17).

9. A steam and lotion dispenser according to claim 8, wherein said member attached to said control means is a valve stem (16) which is surrounded by a path selection member biasing spring (30) and which is slidably and non-rotatably guided in a spring abutment means (22) against which the spring (30) rests at and end thereof remote from the path selection member (13).

10. A steam and lotion dispenser according to claim 6, wherein the control means (17) is mounted for rotation with the hollow body (6) about said one axis of rotation thereof, and is mounted for rotation with respect to the hollow body (6) about a second axis (31) for actuating the valve (13) in the hollow body (6).

11. A steam and lotion dispenser according to claim 10, wherein the control means comprise a handle (17) articulated to a valve stem (17) about said second axis (31), and cam means (33) secured to the handle (17) for displacing the second axis (31) upon rotation of the handle about said second axis (31).

12. A steam and lotion dispenser according to claim 6, comprising a sleeve (4) which surrounds the hollow body around the steam inlet aperture (9) and supports the hollow body (6) for rotation about said one axis, wherein the sleeve (4) and the hollow body (6) define an annular chamber (8) communicating with the steam container (1) through an aperture (5) of the sleeve (4).

* * * * *